US006267595B1

United States Patent
Grätz

(12) 
(10) Patent No.: US 6,267,595 B1
(45) Date of Patent: Jul. 31, 2001

(54) ROTARY TOOL FOR MACHINING WORKPIECES

(75) Inventor: Dieter Grätz, Au (CH)

(73) Assignee: Edenta AG Dentalproducte (CH)

( * ) Notice: Subject to any disclaimer, the term of this patent is extended or adjusted under 35 U.S.C. 154(b) by 0 days.

(21) Appl. No.: 09/544,541

(22) Filed: Apr. 6, 2000

(30) Foreign Application Priority Data

Apr. 12, 1999 (DE) .................................. 199 16 336

(51) Int. Cl.[7] ...................................................... A61C 3/02
(52) U.S. Cl. ........................................... 433/165; 433/166
(58) Field of Search .................................... 433/165, 166

(56) References Cited

U.S. PATENT DOCUMENTS 4,681,541 * 7/1987 Snaper .................................. 433/165
5,543,210 * 8/1996 Kullander et al. .................. 428/217

FOREIGN PATENT DOCUMENTS

3048383 * 7/1982 (DE) .
3842915 * 12/1989 (DE) .

* cited by examiner

Primary Examiner—John J. Wilson
(74) Attorney, Agent, or Firm—Laubscher & Laubscher

(57) ABSTRACT

A rotary tool for material detaching work, especially in dentistry, comprising a machining portion having an outer circumferential surface coated with a nickel layer in which diamond particles are embedded, is characterized in that the nickel layer and the diamond particles protruding from it are covered by a layer of chromium nitride. The duration of the tool is considerably increased by the chromium nitride layer.

3 Claims, 1 Drawing Sheet

Fig. 1
Fig. 2
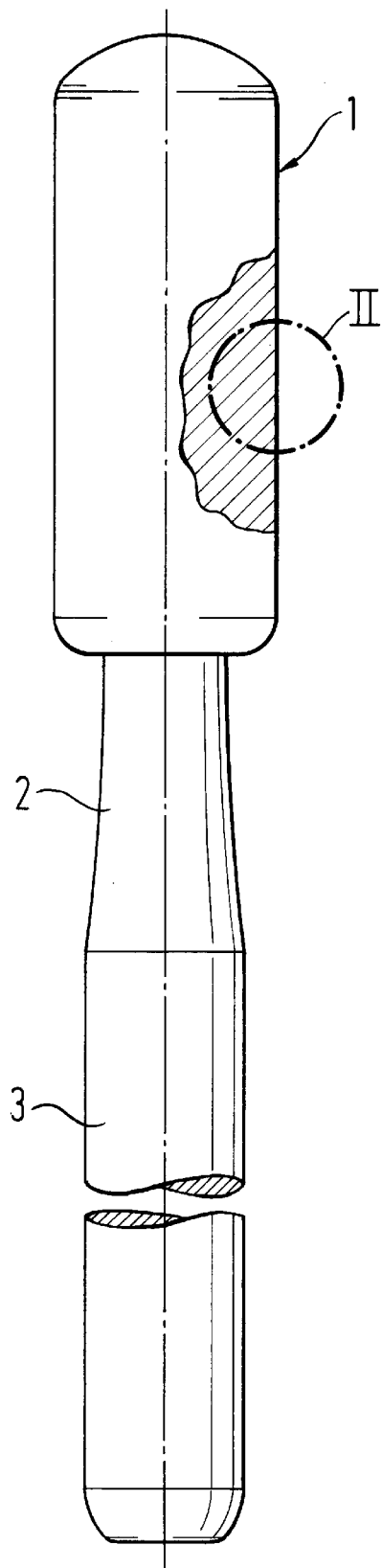
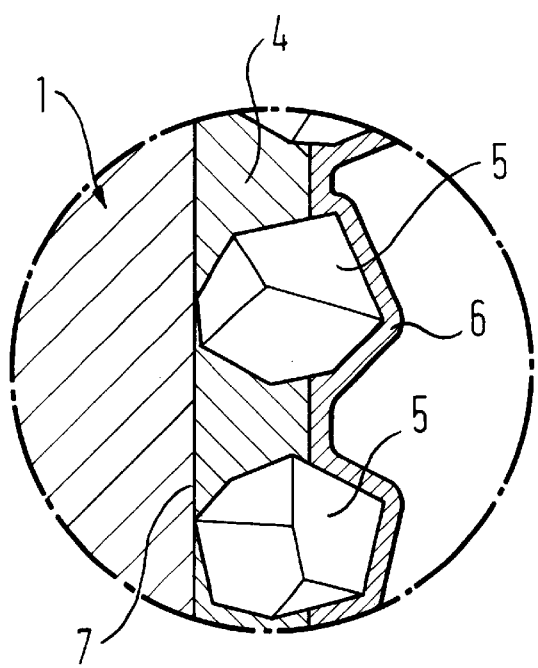

ROTARY TOOL FOR MACHINING WORKPIECES

FIELD OF THE INVENTION

The instant invention relates to a rotary tool for machining workpieces, especially for material detaching work in dentistry, comprising a machining portion having an outer circumferential surface coated with a nickel layer in which diamond particles are embedded.

BACKGROUND OF THE INVENTION

Grinders and similar abravise tools, milling cutters and the like may be named as examples of rotary tools of the kind in question. The nickel layer protects the machining portion from corrosion and bonds the diamond particles to the machining portion. Yet nickel layers are relatively soft and tend to wear easily. During use of the tool, it is the diamond particles which do the cutting work and, therefore, suffer the greatest stress. Even so the stress in the circumferential surface of the machining portion still is great, particularly due to the resulting chips so that the nickel layer wears off in the course of the time of use.

It was found that the wear described of the machining portion may result in loosening of the diamond particles in the nickel layer from which they may become detached, thereby rendering the tool useless.

It is generally known to increase the corrosion resistance and surface hardness of work pieces by providing them with a chromium nitride coat.

SUMMARY OF THE INVENTION

It is the object of the instant invention to design a tool of the kind specified such that its operational life will be extended.

In a tool according to the invention the nickel layer, including the diamond particles embedded therein, is covered by a coat of chromium nitride, whereby not only the wear of the nickel layer is reduced but also the diamond particles are anchored more firmly than before in the nickel layer. The chromium nitride coat, at the same time, fills the ÿuneven surface structure of the diamond particles as well as the gaps separating the nickel layer and the diamond particles. Thus the diamond particles become embedded more firmly. Surprisingly, that has resulted in prolonging the duration of the tool according to the invention by up to four times.

BRIEF DESCRIPTION OF THE DRAWING

The invention will be described in more detail, by way of example, with reference to the accompanying drawings, in which FIG. 1 is a side view, partly shown in section, of a grinding tool according to the invention, presented on an enlarged scale;

FIG. 2 is a part sectional view in the area of the circle at II in FIG. 1, on a further enlarged scale.

DESCRIPTION OF THE PREFERRED EMBODIMENT

Referring now to FIG. 1, the grinding tool comprises a machining portion 1 which is connected by a neck 2 to a clamping shaft 3. The diameter of the neck 2 gradually reduces from the end of the neck 2 that meets the clamping shaft 3 to the end of the neck 2 that meets the machining portion 1, thereby allowing the neck 2 to have a diameter at the point where the neck 2 meets the machining portion 1 that is smaller than at the point where the neck 2 meets the clamping shaft 3. The tool may be clamped in the chuck of a respective dental instrument or device (not shown) by way of the clamping shaft 3.

As shown in FIG. 2, the outer circumferential surface 7 of the machining portion 1 is covered by a nickel layer 4. A plurality of diamond particles 5 are embedded in the nickel layer 4. The diamond particles 5 are contiguous with the circumferential surface of the machining portion and are of such a size as to extend outwardly beyond, and protrude from, the nickel layer 4. The surface areas of the nickel layer located between the diamond particles 5 as well as the surface areas of the diamond particles 5 projecting outwardly from the nickel layer 4 are coated by a thin film 6 of chromium nitride (CrN) having a thickness from 1 to 4 $\mu$m. Due to its increased hardness, this thin film 6 protects the nickel layer 4 from becoming worn prematurely and, at the same time, anchors the diamond particles 5 more firmly in the nickel layer 4 as the thin film 6 penetrates the uneven surface structure in the area of the gaps between the nickel layer 4 and the diamond particles 5. Experiments have shown that the duration or service life of tools made according to the invention exceeds that of known tools by up to four times.

A tool according to the invention is useful not only in dentistry but may be employed also for other precision mechanical machining work. In practice, the diameter of the clamping shaft may be in the order of between 1.0 and 4.0 mm, especially being 1.60, 2.35, or 3 mm. The length of the tool may be in the range between 10 and 60 mm.

The features disclosed in the specification above and in the claims and drawings may be significant for implementing the invention in its various modifications, both individually and in any combination.

What is claimed is:

1. A rotary machining tool for use in the field of dentistry, comprising:
   (a) a clamping shaft portion (3);
   (b) a cylindrical machining head portion (1) arranged collinearly relative to said shaft portion, said head portion having a first end adjacent said clamping shaft portion, and a rounded second end remote from said clamping shaft portion;
   (c) a neck portion (2) connecting said head portion first end with said shaft portion;
   (d) a layer of nickel (4) covering at least the cylindrical circumferential surface of said head portion;
   (e) a plurality of diamond particles (5) embedded in said nickel layer, said particles being in contiguous engagement with said head portion cylindrical surface and protruding outwardly from said nickel layer; and
   (f) a layer of chromium nitride (6) completely covering the protruding portion of said diamond particles and the external surface of said nickel layer, said chromium nitride layer having a thickness of from 1 to 4 $\mu$m, whereby said chromium nitride layer fills the uneven surface structure of the diamond particles as well as any gaps separating said nickel layer and said diamond particles.

2. A rotary machining tool as defined in claim 1, wherein said clamping shaft portion has a diameter between 1.0 and 4.0 mm; and further wherein said neck portion is tapered radially inwardly in the direction of said machining head-portion.

3. A rotary machining tool as defined in claim 2, wherein the length of the tool is between 10 mm and 60 mm.

* * * * *